US007746463B2

(12) United States Patent
Yoo

(10) Patent No.: US 7,746,463 B2
(45) Date of Patent: Jun. 29, 2010

(54) APPARATUS FOR INSPECTING DEFECT OF RUBBING CLOTH AND RUBBING APPARATUS WITH THE SAME

(75) Inventor: Yong-Chul Yoo, Gyeonggi-Do (KR)

(73) Assignee: LG Display Co., Ltd., Seoul (KR)

( * ) Notice: Subject to any disclaimer, the term of this patent is extended or adjusted under 35 U.S.C. 154(b) by 288 days.

(21) Appl. No.: 11/639,341

(22) Filed: Dec. 15, 2006

(65) Prior Publication Data

US 2008/0002196 A1    Jan. 3, 2008

(30) Foreign Application Priority Data

Jun. 30, 2006    (KR)    ...................... 10-2006-0061478

(51) Int. Cl.
G01N 21/00    (2006.01)
G01N 21/84    (2006.01)
G01B 11/28    (2006.01)

(52) U.S. Cl. ...................... 356/238.1; 356/430; 356/630

(58) Field of Classification Search ........................ None
See application file for complete search history.

(56) References Cited

FOREIGN PATENT DOCUMENTS

| JP | 5-241157 | 9/1993 |
|---|---|---|
| JP | 2002-244136 | 8/2002 |
| KR | 639417 B1 * | 11/2006 |
| TW | 589497 | 6/2004 |

* cited by examiner

*Primary Examiner*—Gregory J Toatley, Jr.
*Assistant Examiner*—Amanda H Merlino
(74) *Attorney, Agent, or Firm*—McKenna Long & Aldridge LLP

(57) ABSTRACT

Disclosed are an apparatus for inspecting defect of a rubbing cloth and a rubbing apparatus with the same. The apparatus for inspecting defect of the rubbing cloth includes a housing surrounding the periphery of the rubbing cloth, a transfer unit connected to the upper portion of the housing for transferring the housing along a length direction of a rubbing roll, an illumination unit installed at one side in the housing for illuminating the rubbing cloth, and a camera unit installed at the other side in the housing to correspond to the illumination unit on the basis of the rubbing roll. The apparatus for inspecting defect of the rubbing cloth can rapidly and precisely detect the defect of the rubbing cloth by using the illumination unit and the camera unit.

5 Claims, 4 Drawing Sheets

APPARATUS FOR INSPECTING DEFECT OF RUBBING CLOTH AND RUBBING APPARATUS WITH THE SAME

The present disclosure relates to subject matter contained in priority Korean Application No. 10-2006-0061478, filed on Jun. 30, 2006, which is incorporated by reference for all purposes as if fully incorporated herein.

BACKGROUND OF THE INVENTION

1. Field of the Invention

The present invention relates to an apparatus for inspecting and detecting defects of rubbing cloths and a rubbing apparatus with the same, and more particularly, to an apparatus for inspecting for defects of a rubbing cloth which can rapidly and precisely detect the defect of the rubbing cloth by using a camera, and a rubbing apparatus having the same.

2. Description of the Background Art

With the growth of the information society, a liquid crystal display device, which is one of a variety of information display devices, acquires greater importance.

Notably, the liquid crystal display device has advantages of small size, light weight and low power consumption. The liquid crystal display device has gradually expanded its applications and has become a substitute for a cathode ray tube (CRT) displays.

The liquid crystal display device includes two glass substrates with liquid crystal molecules injected between the two glass substrates.

The alignment of the liquid crystal molecules injected between the two glass substrates is changed according to an external electrical signal, in order to adjust a light transmitting amount into an appropriate amount.

To attain a specific optical effect of the liquid crystal display device, the liquid crystal molecules must be oriented in a specific direction.

In general, the liquid crystal molecules are locally oriented. Therefore, an organic polymer film directly contacting the liquid crystal molecules is artificially formed on an indium-tin oxide (ITO) electrode to orient the liquid crystal molecules to the specific direction desired. This organic polymer film is called an orientation film.

In the manufacturing process of the liquid crystal display, a rubbing process is carried out to form orientation grooves on the surface of the orientation film.

The rubbing process wraps a rubbing cloth made of a synthetic fiber such as rayon or nylon around a roller, and makes the roller contact the orientation film to rub against the surface of the orientation film. As a result, the orientation grooves are formed on the surface of the orientation film with a uni-directional alignment over a predetermined level and a pretilt angle existing in a predetermined range.

In the rubbing process, defects in the rubbing cloth mostly result from a loosened part from the rubbing cloth foreign objects and substances sticking to the rubbing cloth, or non-uniform thickness of the rubbing cloth.

Normally, an inspector inspects the rubbing cloth for the defect by his/her experience. However, it takes a lot of effort and time to inspect the rubbing cloth for the defect.

In addition, each inspector has their own standards for inspecting the rubbing cloth for the defect, which reduces accuracy of the inspection.

SUMMARY OF THE INVENTION

Therefore, an object of the present invention is to provide an apparatus for inspecting defect of a rubbing cloth which can rapidly and precisely detect the defect of the rubbing cloth by using an illumination unit and a camera unit, and a rubbing apparatus with the same.

To achieve these and other advantages and in accordance with the purpose of the present invention, as embodied and broadly described herein, there is provided an apparatus for inspecting for defects of a rubbing cloth including: a housing surrounding the periphery of the rubbing cloth; a transfer unit connected to the upper portion of the housing for transferring the housing along a length direction of a rubbing roll; an illumination unit installed at one side in the housing for illuminating the rubbing cloth; and a camera unit installed at the other side in the housing to correspond to the illumination unit on the basis of the rubbing roll.

For example, the transfer unit is a device for transferring the housing, and includes rails installed on a table, wheels contacting the rails, and a wheel driving motor for driving the wheels.

For example, the camera unit includes: an upper camera for photographing the top end of the rubbing cloth; a lower camera for photographing the bottom end of the rubbing cloth; and an intermediate camera for photographing the intermediate portion of the rubbing cloth.

According to another aspect of the present invention, there is provided a rubbing apparatus including: a table for supporting a substrate; a rubbing roll rotatably installed on the top surface of the table, a rubbing cloth being wrapped round the outer circumference of the rubbing roll; and an apparatus for inspecting the rubbing cloth installed on the table to be movable along the length direction of the rubbing roll for inspecting the rubbing cloth for a defect.

According to yet another aspect of the present invention, there is provided a method for inspecting a defect of a rubbing cloth including: preparing an apparatus for inspecting a rubbing cloth and a rubbing apparatus; providing the rubbing cloth; illuminating the rubbing cloth by using an illumination unit disposed at the apparatus for inspecting the rubbing cloth; and measuring the thickness of the rubbing cloth by using a camera unit disposed at the apparatus for inspecting the rubbing cloth.

According to yet another aspect of the present invention, there is provided a method for inspecting defect of a rubbing cloth including: preparing an apparatus for inspecting a rubbing cloth and a rubbing apparatus; providing the rubbing cloth; illuminating the rubbing cloth by using an illumination unit disposed at the apparatus for inspecting the rubbing cloth; measuring the thickness of the rubbing cloth by measuring the thickness from one end to another end of the rubbing cloth at an upper of a rubbing roll by using an upper camera disposed at the apparatus for inspecting the rubbing cloth, and measuring the thickness from one end to another end of the rubbing cloth at a bottom of a rubbing roll by using a lower camera; and detecting a loosened part from the rubbing cloth according to the thickness of the rubbing cloth.

According to yet another aspect of the present invention, there is provided a method for inspecting defect of a rubbing cloth including: preparing an apparatus for inspecting a rubbing cloth and a rubbing apparatus; providing the rubbing cloth; illuminating the rubbing cloth by using an illumination unit disposed at the apparatus for inspecting the rubbing cloth; and detecting foreign objects and substances sticking to the rubbing cloth in every predetermined section, and detecting the portion stained with foreign objects and substances due to cloth scouring on the basis of the gray scale, by using an intermediate camera disposed at the apparatus for inspecting the rubbing cloth.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Reference will now be made in detail to embodiments of the present invention, examples of which are illustrated in the accompanying drawings.

Figure 1:
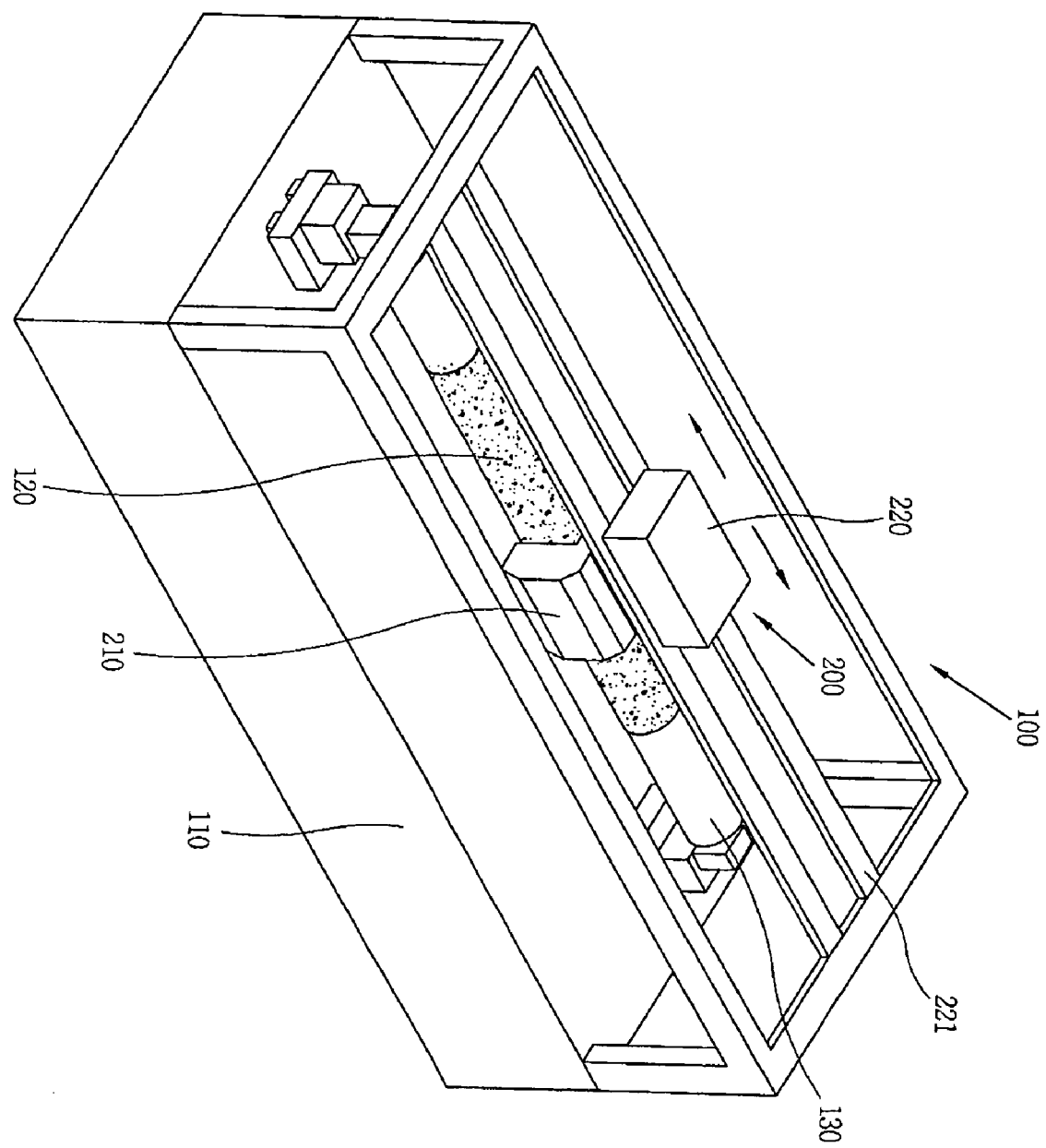
FIG. 1 is a perspective view illustrating an apparatus for inspecting a rubbing cloth for a defect and a rubbing apparatus in accordance with the present invention.

FIG. 1 is a perspective view illustrating an apparatus for inspecting defect of a rubbing cloth and a rubbing apparatus in accordance with the present invention.

Figure 2:
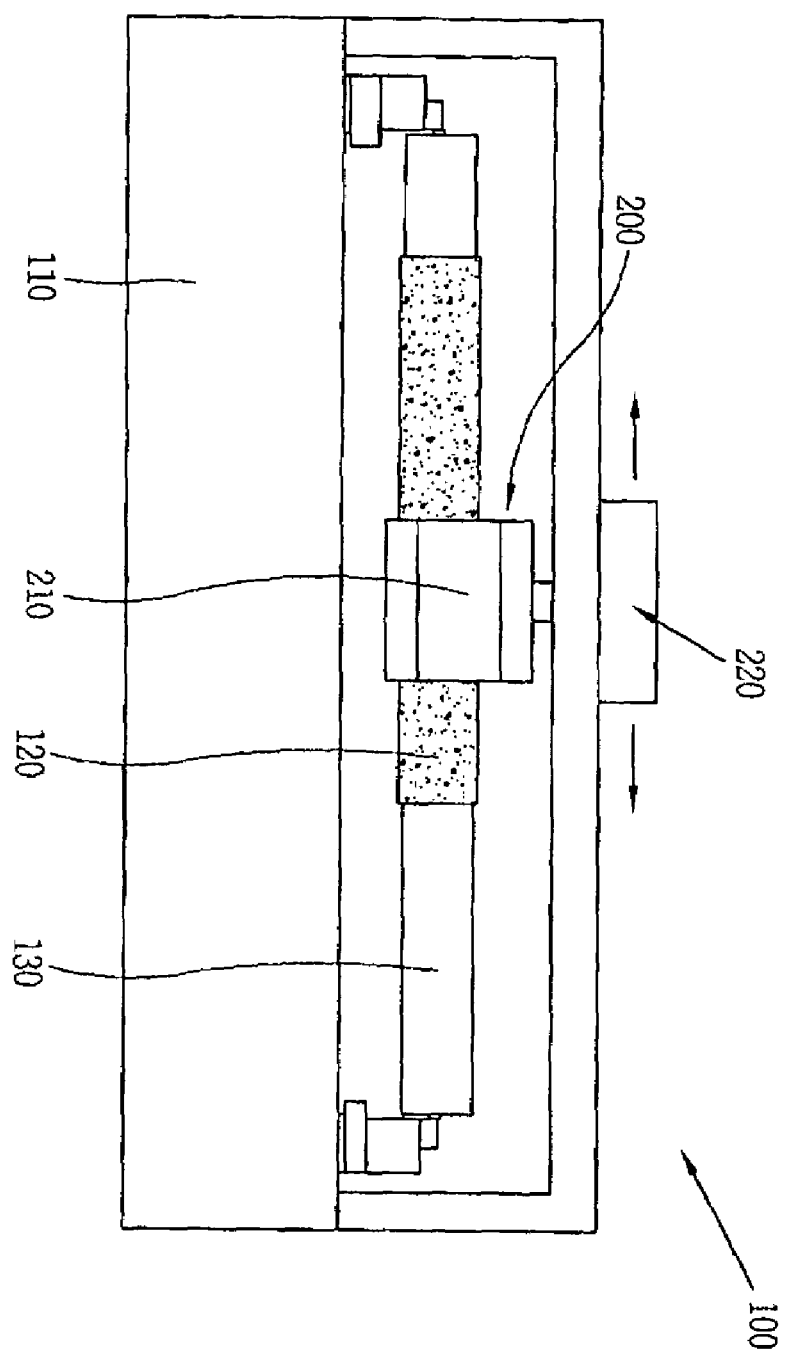
FIG. 2 is a front-sectional view illustrating the apparatus for inspecting the rubbing cloth for the defect in FIG. 1.

FIG. 2 is a front-sectional view illustrating the apparatus for inspecting defect of the rubbing cloth in FIG. 1.

Figure 3:
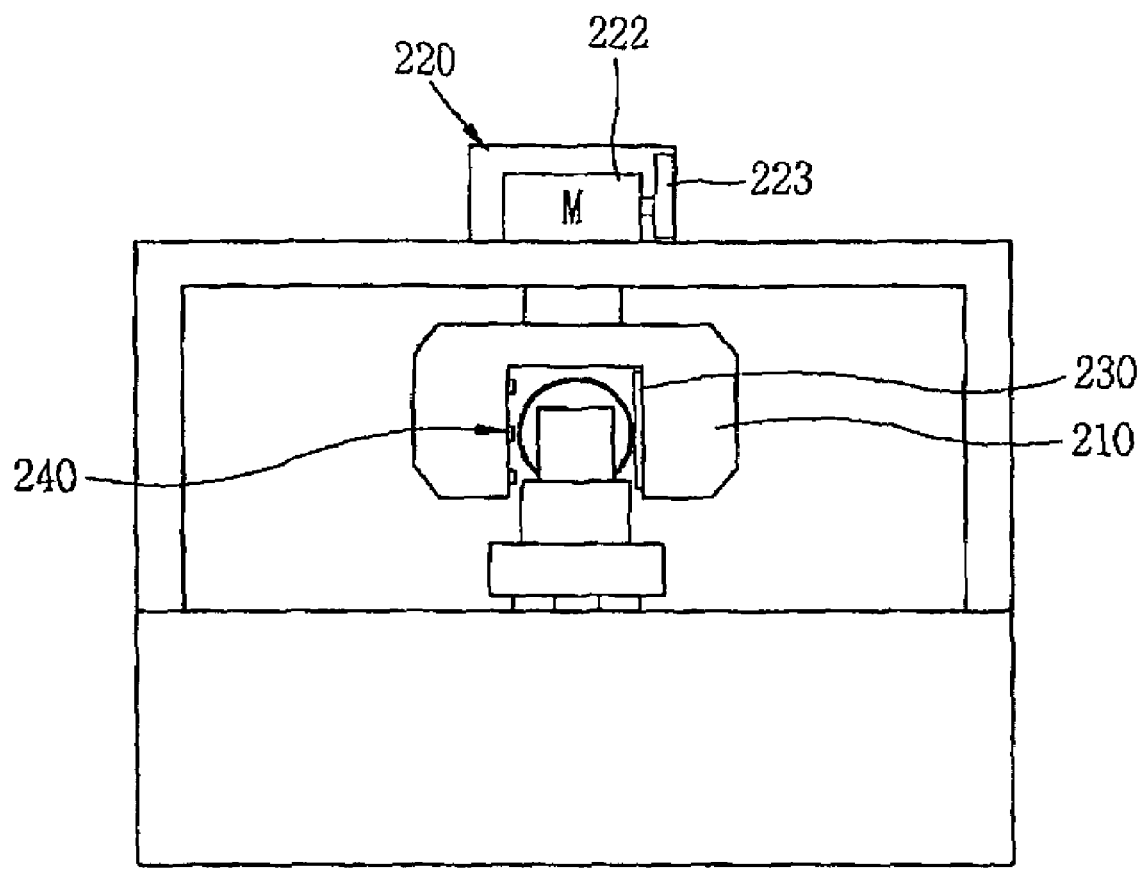
FIG. 3 is a side-sectional view illustrating the apparatus for inspecting the rubbing cloth for the defect in FIG. 1.

FIG. 3 is a side-sectional view illustrating the apparatus for inspecting defect of the rubbing cloth in FIG. 1.

Referring to FIG. 1, the rubbing apparatus 100 includes a table 110 for supporting a substrate, a rubbing roll 130 rotatably installed on the top surface of the table 110, a rubbing cloth 120 being wrapped round the outer circumference of the rubbing roll 130, and the apparatus 200 for inspecting the rubbing cloth 120 installed on the table 110 to be movable along the length direction of the rubbing roll 130 for inspecting the rubbing cloth 120 for the defect.

As illustrated in FIG. 2, the apparatus 200 for inspecting the rubbing cloth 120 for the defect includes a housing 210 for surrounding the periphery of the rubbing cloth 120, a transfer unit 220 connected to the upper portion of the housing 210 for transferring the housing 210 along the length direction of the rubbing roll 130, an illumination unit 230 installed at one side in the housing 210 for illuminating the rubbing cloth 120, and a camera unit 240 installed at the other side in the housing 210 to correspond to the illumination unit 230 on the basis of the rubbing roll 130.

The transfer unit 220, which is a device for transferring the housing 210, includes rails 221 (refer to FIG. 1) installed on the table 110, wheels 223 contacting the rails 221, and a wheel driving motor 222 for driving the wheels 223.

As shown in FIG. 3, the camera unit 240 includes an upper camera 241 for photographing the top end of the rubbing cloth 120, a lower camera 242 for photographing the bottom end of the rubbing cloth 120, and an intermediate camera 243 for photographing the intermediate portion of the rubbing cloth 120.

The operation method of the apparatus for inspecting defect of the rubbing cloth in accordance with the present invention will now be described with reference to FIG. 4.

Figure 4:
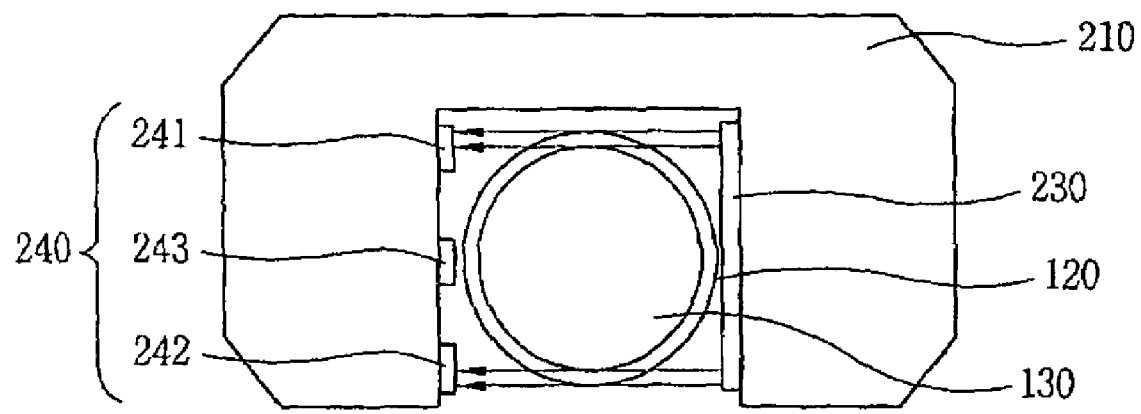
FIG. 4 is a using state view illustrating the apparatus for inspecting the rubbing cloth for the defect for explaining the inspection of the thickness of the rubbing cloth, a loosened part from the rubbing cloth, and foreign objects and substances sticking to the rubbing cloth.

FIG. 4 is provided to illustrate inspection of the thickness of the rubbing cloth, a loosened part from the rubbing cloth, and foreign objects and substances sticking to the rubbing cloth.

First, the operation method of the apparatus 200 for inspecting the rubbing cloth 120 measures the thickness of the rubbing cloth 120. When the illumination unit 230 illuminates the rubbing cloth 120, the upper camera 214 measures the thickness from one end to another end of the rubbing cloth 120 at an upper of the rubbing roll 130, and the lower camera 242 measures the thickness from one end to another end of the rubbing cloth 120 at a bottom of the rubbing roll 130, thereby measuring the thickness of the rubbing cloth 120.

The diameter of the rubbing roll 130 is a predetermined, known quantity. Accordingly, the thickness of the rubbing cloth 120 can be easily precisely obtained by subtracting the value of the rubbing cloth 120 from the values measured by the upper camera 241 and the lower camera 242.

Second, the operation method of the apparatus 200 for inspecting the rubbing cloth 120 detects the loosened part from the rubbing cloth 120. When the illumination unit 230 illuminates the rubbing cloth 120, the upper camera 214 measures the thickness from one end to another end of the rubbing cloth 120 at an upper of the rubbing roll 130, and the lower camera 242 measures the thickness from one end to another end of the rubbing cloth 120 at a bottom of the rubbing roll 130, thereby measuring the thickness of the rubbing cloth 120 and detecting the loosened part from the rubbing cloth 120.

At last, the operation method of the apparatus 200 for inspecting the rubbing cloth 120 detects foreign objects and substances sticking to the rubbing cloth 120. When the illumination unit 230 illuminates the rubbing cloth 120, the intermediate camera 243 detects foreign objects and substances sticking to the rubbing cloth 120.

This method detects foreign objects and substances in every 12 mm×8 mm section, and detects the portion stained with foreign objects and substances due to cloth scouring on the basis of the gray scale.

The whole rubbing cloth 120 can be inspected by rotating the rubbing roll 130, and transferring the apparatus 200 for inspecting the rubbing cloth 120 for the defect by the transfer unit 220 at the same time. When the wheels 223 are rotated by the rotation of the driving motor 222, the wheels 223 move along the rails 221 to transfer the apparatus 200 for inspecting the rubbing cloth 120.

As discussed earlier, in accordance with the present invention, the apparatus for inspecting the rubbing cloth for the defect and the rubbing apparatus having the same have the following advantages.

The apparatus for inspecting the rubbing cloth for the defect and the rubbing apparatus having the same can rapidly and precisely detect the defect of the rubbing cloth by using the illumination unit and the camera unit.

In addition, the apparatus for inspecting the rubbing cloth for the defect and the rubbing apparatus having the same can establish the objective standard for inspecting the rubbing cloth for the defect.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

What is claimed is:

1. An apparatus for inspecting defect of a rubbing cloth, comprising:
   a housing surrounding the periphery of the rubbing cloth;
   a transfer unit connected to the upper portion of the housing for transferring the housing along a length direction of a rubbing roll, wherein the transfer unit comprises rails installed on a table; wheels contacting the rails; and a wheel driving motor for driving the wheels, and wherein when the rubbing roll is rotated for inspecting defect of the rubbing cloth, the housing is transferred by the transfer unit at the same time, and when the wheels are rotated by the rotation of the driving motor, the wheels move along the rails to transfer the housing;
   an illumination unit installed at one side in the housing for illuminating the rubbing cloth; and
   a camera unit installed at the other side in the housing to correspond to the illumination unit on the basis of the rubbing roll, wherein the camera unit comprises an upper camera for photographing the top end of the rubbing cloth; a lower camera for photographing the bottom end of the rubbing cloth; and an intermediate camera for photographing the intermediate portion of the rubbing cloth.

2. A rubbing apparatus having an apparatus for inspecting a rubbing cloth for a defect, comprising:
   a table for supporting a substrate;
   a rubbing roll rotatably installed on the top surface of the table, a rubbing cloth being wrapped round the outer circumference of the rubbing roll; and
   a apparatus for inspecting the rubbing cloth installed on the table
   wherein the apparatus for inspecting the rubbing cloth comprises: a housing surrounding the periphery of the rubbing cloth; a transfer unit connected to the upper portion of the housing for transferring the housing along a length direction of a rubbing roll, wherein the transfer unit comprises rails installed on a table, wheels contacting the rails and a wheel driving motor for driving the wheels, wherein when the rubbing roll is rotated for inspecting defect of the rubbing cloth, the housing is transferred by the transfer unit at the same time, and when the wheels are rotated by the rotation of the driving motor, the wheels move along the rails to transfer the housing; an illumination unit installed at one side in the housing for illuminating the rubbing cloth; and a camera unit installed at the other side in the housing to correspond to the illumination unit on the basis of the rubbing roll, wherein the camera unit comprises an upper camera for photographing the top end of the rubbing cloth, a lower camera for photographing the bottom end of the rubbing cloth and an intermediate camera for photographing the intermediate portion of the rubbing cloth.

3. A method for inspecting defect of a rubbing cloth, comprising:
   preparing an apparatus for inspecting a rubbing cloth and a rubbing apparatus;
   providing the rubbing cloth;
   illuminating the rubbing cloth by using an illumination unit disposed at the apparatus for inspecting the rubbing cloth, wherein the apparatus for inspecting the rubbing cloth comprises a housing surrounding the periphery of the rubbing cloth; a transfer unit connected to the upper portion of the housing for transferring the housing along a length direction of a rubbing roll, wherein the transfer unit comprises rails installed on a table, wheels contacting the rails and a wheel driving motor for driving the wheels, and wherein when the rubbing roll is rotated for inspecting defect of the rubbing cloth, the housing is transferred by the transfer unit at the same time, and when the wheels are rotated by the rotation of the driving motor, the wheels move along the rails to transfer the housing;
   measuring the thickness of the rubbing cloth by using a camera unit disposed at
   the apparatus for inspecting the rubbing cloth, wherein measuring the thickness of the rubbing cloth is performed by measuring the thickness from one end to another end of the rubbing cloth at an upper of a rubbing roll by using an upper camera disposed at the apparatus for inspecting the rubbing cloth, and measuring the thickness from one end to another end of the rubbing cloth at a bottom of a rubbing roll by using a lower camera; and
   detecting the thickness of the rubbing cloth by subtracting a rubbing cloth value from the values measured by the upper camera and the lower camera.

4. A method for inspecting defect of a rubbing cloth, comprising:
   preparing an apparatus for inspecting a rubbing cloth and a rubbing apparatus;
   providing the rubbing cloth;
   illuminating the rubbing cloth by using an illumination unit disposed at the apparatus for inspecting the rubbing cloth;
   measuring the thickness of the rubbing cloth by measuring the thickness from one end to another end of the rubbing cloth at an upper of a rubbing roll by using an upper camera disposed at the apparatus for inspecting the rubbing cloth, and measuring the thickness from one end to another end of the rubbing cloth at a bottom of a rubbing roll by using a lower camera, wherein the apparatus for inspecting the rubbing cloth comprises a housing surrounding the periphery of the rubbing cloth; a transfer unit connected to the upper portion of the housing for transferring the housing along a length direction of a rubbing roll, wherein the transfer unit comprises rails installed on a table, wheels contacting the rails and a wheel driving motor for driving the wheels, and wherein when the rubbing roll is rotated for inspecting defect of the rubbing cloth, the housing is transferred by the transfer unit at the same time, and when the wheels are rotated by the rotation of the driving motor, the wheels move along the rails to transfer the housing; an illumination unit installed at one side in the housing for illuminating the rubbing cloth; and a camera unit installed at the other side in the housing to correspond to the illumination unit on the basis of the rubbing roll, wherein the camera unit comprises an upper camera for photographing the top end of the rubbing cloth, a lower camera for photographing the bottom end of the rubbing cloth and an intermediate camera for photographing the intermediate portion of the rubbing cloth; and
   detecting a loosened part from the rubbing cloth according to the thickness of the rubbing cloth.

5. A method for inspecting defect of a rubbing cloth, comprising:
   preparing an apparatus for inspecting a rubbing cloth and a rubbing apparatus;

providing the rubbing cloth;

illuminating the rubbing cloth by using an illumination unit disposed at the apparatus for inspecting the rubbing cloth, wherein the apparatus for inspecting the rubbing cloth comprises a housing surrounding the periphery of the rubbing cloth; a transfer unit connected to the upper portion of the housing for transferring the housing along a length direction of a rubbing roll, wherein the transfer unit comprises rails installed on a table, wheels contacting the rails and a wheel driving motor for driving the wheels, and wherein when the rubbing roll is rotated for inspecting defect of the rubbing cloth, the housing is transferred by the transfer unit at the same time, and when the wheels are rotated by the rotation of the driving motor, the wheels move along the rails to transfer the housing; an illumination unit installed at one side in the housing for illuminating the rubbing cloth; and a camera unit installed at the other side in the housing to correspond to the illumination unit on the basis of the rubbing roll, wherein the camera unit comprises an upper camera for photographing the top end of the rubbing cloth, a lower camera for photographing the bottom end of the rubbing cloth and an intermediate camera for photographing the intermediate portion of the rubbing cloth; and detecting foreign objects and substances sticking to the rubbing cloth in every predetermined section, and detecting the portion stained with foreign objects and substances due to cloth scouring on the basis of the gray scale, by using the intermediate camera disposed at the apparatus for inspecting the rubbing cloth, wherein the intermediate camera photographs the intermediate portion of the rubbing cloth.

* * * * *